United States Patent [19]

Freenor, III

[11] 4,025,585

[45] May 24, 1977

[54] S,S-DIALKYL-N-SUBSTITUTED PHOSPHOROAMIDODITHIONITES

[75] Inventor: Francis J. Freenor, III, Richmond, Calif.

[73] Assignee: Chevron Research Company, San Francisco, Calif.

[22] Filed: Mar. 1, 1976

[21] Appl. No.: 662,313

Related U.S. Application Data

[62] Division of Ser. No. 565,924, April 7, 1975, Pat. No. 3,959,271, which is a division of Ser. No. 466,433, May 2, 1974, Pat. No. 3,886,238, which is a division of Ser. No. 219,559, Jan. 20, 1972, Pat. No. 3,832,424.

[52] U.S. Cl. .................................. 260/956; 71/87; 260/959; 424/200
[51] Int. Cl.² ....................... C07F 9/24; A01N 9/36
[58] Field of Search ............................ 260/956, 959

[56] References Cited

UNITED STATES PATENTS 3,136,784  6/1964  Beriger .......................... 260/959 X

*Primary Examiner*—Anton H. Sutto
*Attorney, Agent, or Firm*—J. A. Buchanan, Jr.; Dix A. Newell; Raymond Owyang

[57] ABSTRACT

Compounds of the formula

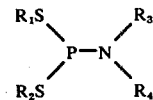

wherein $R_1$ and $R_2$ are independently alkyl of 1 to 8 carbon atoms, or alkenyl of 2 to 8 carbon atoms, $R_3$ is hydrogen or alkyl of 1 to 4 carbon atoms, and $R_4$ is hydrogen, alkyl of 1 to 4 carbon atoms, alkenyl of 2 to 4 carbon atoms, aryl of 6 to 15 carbon atoms optionally substituted with halogen atoms or alkyl groups of 1 to 4 carbon atoms or an acyl group of 2 to 4 carbon atoms, with the proviso that $R_3$ and $R_4$ may be joined to form an alkylene radical of 2 to 5 carbon atoms. The compounds possess insecticidal and herbicidal activity.

6 Claims, No Drawings

S,S-DIALKYL-N-SUBSTITUTED PHOSPHOROAMIDODITHIONITES

This is a division of application Ser. No. 565,924, filed Apr. 7, 1975, now U.S. Pat. No. 3,959,271, which in turn, is a division of application Ser. No. 466,433, filed May 2, 1974, now U.S. Pat. No. 3,886,238, which in turn is a division of application Ser. No. 219,559, filed Jan. 20, 1972, now U.S. Pat. 2,832,424.

BACKGROUND OF THE INVENTION

1. Field

The present invention is directed to phosphoroamidodithionites, more particularly S,S-dialkyl-N-mono- and di-substituted phosphoroamidothionites and their use as insecticides and/or herbicides.

2. Description of the Invention

Compounds of the present invention may be represented by the formula

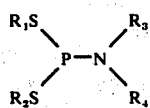

wherein $R_1$ and $R_2$ are independently alkyl of 1 to 8 carbon atoms, preferably alkyl of 1 to 4 carbon atoms and more preferably alkyl of 3 to 4 carbon atoms, or alkenyl of 2 to 8 carbon atoms, preferably alkenyl of 2 to 4 carbon atoms, $R_3$ is hydrogen or alkyl of 1 to 4 carbon atoms, $R_4$ is hydrogen, alkyl of 1 to 4 carbon atoms, alkenyl of 2 to 4 carbon atoms, aryl of 6 to 15 carbon atoms substituted with 0 to 5 halogen atoms of atomic number 9 to 35 or alkyl groups of 1 to 4 carbon atoms, or an acyl group of 2 to 4 carbon atoms, with the proviso that $R_3$ and $R_4$ may be joined to form an alkylene radical of 2 to 5 carbon atoms, preferably 4 to 5 carbon atoms.

The aryl groups which $R_4$ may represent are preferably benzyl or phenyl, either being substituted with 0 to 5 halogen atoms of atomic number 9 to 35 or alkyl groups of 1 to 4 carbon atoms. More preferably, $R_4$ is phenyl substituted with 0 to 2 halogen atoms of atomic number 9 to 17 or alkyl of 1 to 2 carbon atoms, and still more preferably, phenyl substituted with 0 to 1 chlorine or fluorine atom.

Representative alkyl groups which $R_1$, $R_2$, $R_3$ and $R_4$ may represent include methyl, ethyl, n-propyl, isopropyl, butyl, t-butyl, etc. Representative alkenyl groups which $R_1$, $R_2$ and $R_4$ may represent include vinyl, allyl, crotyl, etc. $R_1$ and $R_2$ may also be pentyl, hexyl, octyl, etc. Preferably $R_1$ and $R_2$ will be the same, or will be alkyl. $R_4$ is preferably alkyl or aryl optionally substituted as the case may be.

Representative aryl groups which $R_4$ may represent include phenyl, naphthyl, benzyl, o-chlorophenyl, o-fluorophenyl, o-bromophenyl, p-fluorophenyl, m-chlorophenyl, o-methylphenyl, p-butylphenyl, o-butylphenyl, o,p-dichlorophenyl, pentachlorophenyl, o-chloro-p-methylphenyl, o-fluoro-m-chlorophenyl, 2-chloronapthyl, etc.

Representative radicals which $R_3$ and $R_4$ joined together with nitrogen may represent include piperidyl, pyrrolidyl and morpholine.

Representative acyl groups which $R_4$ may represent include acetyl, propionyl and butyryl.

Representative compounds of the present invention include S,S-dimethyl-N-butyl phosphoroamidodithionite, S,S,-dimethyl-N-phenyl phosphoroamidodithionite, S,S-diethyl-N,N-dimethyl phosphoroamidodithionite, S,S-dimethyl-N-acetyl phosphoroamidodithionite, S-methyl-S-ethyl-N-isopropyl phosphoroamidodithionite, S-methyl-S-ethyl-N-vinyl phosphoroamidodithionite, S,S-diethyl-N,N-diethyl phosphoroamidodithionite, S,S-diisopropyl-N-methyl phosphoroamidodithionite, S,S-n-butyl phosphoroamidodithionite, S-methyl-S-hexyl-N-ethyl-N-propionyl phosphoroamidodithionite, S-propyl-S-allyl-N-methyl-N-phenyl phosphoroamidodithionite, S-methyl-S-vinyl-N-methyl phosphoroamidodithionite, S,S-dipropyl-N-2-chlorophenyl phosphoroamidodithionite, S,S-dibutyl-N-2,4-dichlorophenyl phosphoroamidodithionite, S,S-dibutyl-N-2-ethylphenyl phosphoroamidodithionite, S,S-diethyl-N-ethyl-N-2-naphthyl phosphoroamidodithionite, S,S-dibutyl-N-pentachlorophosphoroamidodithionite, S,S-dibutyl-N-2,4-dichloro-3,5-dimethylphenyl phosphoroamidodithionite, S,S-dibutyl-N-piperidyl phosphoroamidodithionite, S,S-dibutyl-N-pyrrolidyl phosphoroamidodithionite, etc.

The compounds of the present invention are prepared by the reaction of an appropriate S,S-dialiphatic hydrocarbyl phosphorus halide with ammonia with a suitable amine or with an appropriate amide according to the following reaction:

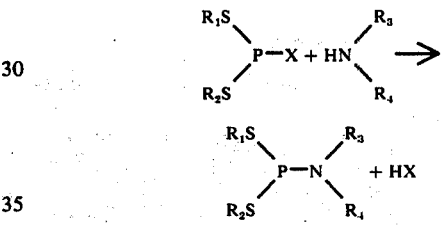

wherein $R_1$, $R_2$, $R_3$ and $R_4$ are as indicated above and X is a halogen, preferably chlorine.

Generally, the reaction is accomplished by adding the ammonia or amine slowly to the phosphorus chloride. Preferably an excess, e.g., up to twice the molar amount of ammonia, amide or the amine can be used. The excess reactant acts as a base acceptor to react with the evolved HX and thereby neutralize it. The reaction is preferably carried out in the presence of an inert solvent, such as methylene chloride ether, benzene, hexane, etc. Also a molecular seive is preferably present which serves as a drying agent for the solvent amine. The amount of molecular seive should be enough to assure substantially complete removal of any $H_2O$.

When ammonia is reacted with the phosphorus chloride it is generally preferable to dissolve the ammonia in the solvent and then add the phosphorus chloride to the ammonia-solvent mixture. When an amine is used, the solvent is preferably added to the phosphorus chloride and the amine added slowly to the phosphorus chloride-solvent mixture.

The above reaction is preferably carried out at a temperature from $-78°$ to $30°$ C. Following the reaction, the product can be recovered by conventional means. Thus the reaction mixture may be stripped of solvent, the product washed with water and dried over magnesium sulfate.

The phosphorus chloride is known in the art and can be prepared as for example by the procedure in U.S. Pat. No. 3,210,244. Thus a suitable mercaptan may be reacted with phosphorus trichloride to give the S,S-dialiphatic hydrocarbyl phosphorus chloride. If different alkyl or alkenyl groups are desired, two different mercaptans can be reacted with the phosphorus trichloride.

The present invention can be more fully understood by reference to the following examples.

EXAMPLE 1

Preparation of S,S-di-n-butyl phosphoroamidodithionite

Ammonia (large excess based on the amount of S,S-dibutyl phosphorus chloride) was dissolved in methylene dichloride, cooled to dry ice temperature. A small number of molecular sieves were added. S,S-dibutyl phosphorus chloride, 6.5 g. (0.03 mole), was then added slowly. A solid white precipitate resulted. The reaction mixture was slowly warmed up to room temperature and left standing approximately 48 hours. The white solid was removed and the remaining solution stripped to obtain an oil having the following analysis:

|   |   | Calculated | Found |
|---|---|---|---|
| N | % | 6.2 | 5.5 |

EXAMPLE 2

Preparation of S,S-di-n-butyl-N,N-diethyl phosphoroamidodithionite 100 ml. of methylene dichloride plus a small amount of molecular sieves were mixed with 13.05 g. of S,S-di-n-butyl phosphorus chloride. Diethyl amine (7.8 g.) was added slowly. The resulting slurry was allowed to stand for approximately 24 hours. The resulting mixture was filtered and stripped to obtain a colorless oil which on chemical analysis showed:

|   |   | Calculated | Found |
|---|---|---|---|
| S | % | 22.8 | 21.7 |
| P | % | 11.01 | 11.8 |

EXAMPLE 3

Preparation of S,S-di-n-butyl-N-pyrrolidyl phosphoroamidodithionite 5.84 g. (0.024 mole) of S,S-di-n-butyl phosphorus chloride was dissolved in approximately 150 ml. of methylene dichloride. A small number of molecular sieves were added. Piperidine, 4.06 g. (0.05 mole) was added slowly. The reaction mixture was cooled in an ice bath during the reaction. The reaction mixture was permitted to stand overnight after which it was filtered and evaporated down to obtain a yellow oil which was then dissolved in methylene dichloride, washed twice with water and dried over magnesium sulfate. After isolation, the chemical analysis showed:

|   |   | Calculated | Found |
|---|---|---|---|
| S | % | 21.8 | 22.1 |
| P | % | 10.6 | 10.4 |

EXAMPLE 4

Preparation of S,S-di-n-butyl-N-acetyl phosphoroamidodithionite

Under a nitrogen atmosphere, 50 ml. of diethyl ether was dried over several molecular sieves. Then, 9.15 g. (0.0373 mole) of S,S-di-n-butyl phosphorus chloride was added to the dry ether. Next, 2.21 g. (0.0373 mole) of acetamide was added and the reaction mixture turned cloudy. Triethylamine, 3.78 g. (0.0373 mole) was added dropwise. A white precipitate formed, and the reaction mixture was stirred for 1 hour at ambient temperature. After warming, the reaction mixture was stirred for 24 hours.

The white precipitate was removed by filtration. The resulting solution slowly formed two layers. After 30 days the layers were separated. The upper layer weighed 5.30 grams. Analysis:

|   |   | Calculated | Found |
|---|---|---|---|
| S | % | 24.0 | 26.3 |
| P | % | 11.6 | 13.8 |

The NMR spectra was consistent with the assigned structure. The infrared spectra had adsorption peaks at 5.85, 6.85, 7.25, 7.85, 8.1, 8.3 and 13.4 microns.

Other compounds of the present invention were prepared substantially as described above and are reported in Table I. All of the compounds are oils.

TABLE I

| Ex. No. | Compound | Elemental Analysis - % | | | | | |
|---|---|---|---|---|---|---|---|
|   |   | S | | P | | Halogen | |
|   |   | Calculated | Found | Calculated | Found | Calculated | Found |
| 5 | S,S-n-butyl-N,N-di-n-propyl phosphoroamidodithionite | 20.7 | 20.7 | 10.0 | 10.0 | — | — |
| 6 | S,S-di-n-butyl-N,N-dimethyl phosphoroamidodithionite | 25.3 | 25.1 | 12.2 | 11.8 | — | — |
| 7 | S,S-di-n-butyl-N-methyl phosphoroamidodithionite | 5.8* | 5.3* | — | — | — | — |
| 8 | S,S-di-n-butyl-N,N-di-n-butyl phosphoroamidodithionite | 19.0 | 19.0 | 9.2 | 8.8 | — | — |
| 9 | S,S-diisopropyl-N,N-diethyl phosphoroamidodithionite | — | — | 12.2 | 11.8 | — | — |
| 10 | S,S-diisopropyl-N,N-di-N-propyl phosphoroamidodithionite | 22.8 | 22.3 | 11.0 | 10.6 | — | — |
| 11 | S,S-di-n-butyl-N-4-chlorophenyl phosphoroamidodithionite | 10.6** | 10.5** | — | — | — | — |
| 12 | S,S-di-n-butyl-N-2-fluorophenyl phosphoroamidodithionite | 6.0** | 6.2** | — | — | — | — |
| 13 | S,S-diisopropyl-N-4-chlorophenyl phosphoroamidodithionite | 11.5** | 9.8* | 10.1 | 9.2 | — | — |
| 14 | S,S-diisopropyl-N-2-fluorophenyl | 22.0 | 21.8 | 11.6 | 11.0 | — | — |

TABLE I-continued

| Ex. No. | Compound | Elemental Analysis - % | | | | | |
|---|---|---|---|---|---|---|---|
| | | S | | P | | Halogen | |
| | | Calculated | Found | Calculated | Found | Calculated | Found |
| | phosphoroamidodithionite | | | | | | |
| 15 | S,S-diisopropyl-N,N-di-n-butyl phosphoroamidodithionite | 20.7 | 18.6 | 10.0 | 9.2 | — | — |
| 16 | S,S-diisopropyl phosphoroamidodithionite | 7.1* | 6.6* | — | — | — | — |
| 17 | S,S-diisopropyl-N-methyl phosphoroamidodithionite | 6.6* | 6.1* | — | — | — | — |
| 18 | S,S-diisopropyl-N-ethyl phosphoroamidodithionite | 28.5 | 27.0 | 13.7 | 12.8 | — | — |
| 19 | S,S-diisopropyl-N-n-butyl phosphoroamidodithionite | 25.3 | 23.8 | 12.2 | 11.6 | — | — |
| 20 | S,S-diethyl-N,N-diethyl phosphoroamidodithionite | 28.5 | 25.6 | 13.8 | 13.0 | — | — |
| 21 | S,S-diethyl-N,N-di-n-butyl phosphoroamidodithionite | 28.5 | 25.4 | 13.8 | 12.1 | — | — |
| 22 | S,S-diethyl-N,N-dimethyl phosphoroamidodithionite | 32.5 | 30.0 | 15.7 | 14.9 | — | — |
| 23 | S,S-diethyl-N-ethyl phosphoroamidodithionite | 32.5 | 29.6 | 15.7 | 14.6 | — | — |
| 24 | S,S-di-n-butyl-N-benzyl phosphoroamidodithionite | 20.4 | 18.4 | 9.8 | 9.1 | — | — |
| 25 | S,S-di-n-butyl-N-allyl phosphoroamidodithionite | 24.2 | 21.9 | 11.7 | 10.6 | — | — |
| 26 | S,S-di-n-propyl-N,N-diethyl phosphoroamidodithionite | 25.3 | 23.6 | 12.2 | 11.3 | — | — |
| 27 | S,S-di-n-propyl-N-n-butyl phosphoroamidodithionite | 25.3 | 25.1 | 12.2 | 11.3 | — | — |
| 28 | S,S-di-n-propyl-N,N-dimethyl phosphoroamidodithionite | 28.5 | 27.5 | 13.8 | 12.5 | — | — |
| 29 | S,S-di-n-propyl-N-methyl phosphoroamidodithionite | 30.4 | 30.3 | 14.6 | 14.8 | — | — |
| 30 | S,S-di-n-propyl-N-piperidyl phosphoroamidodithionite | 24.2 | 21.9 | 11.7 | 10.6 | — | — |
| 31 | S,S-di-n-propyl-N,N-di-n-propyl phosphoroamidodithionite | 22.8 | 21.1 | 11.0 | 10.4 | — | — |
| 32 | S,S-di-n-propyl-N-benzyl phosphoroamidodithionite | 22.3 | 22.5 | 10.8 | 10.4 | — | — |
| 33 | S,S-di-n-propyl-N-allyl phosphoroamidodithionite | 27.1 | 23.9 | 13.1 | 13.0 | — | — |
| 34 | S,S-di-n-propyl-N-2-fluorophenyl phosphoroamidodithionite | 22.0 | 20.0 | 10.6 | 10.5 | — | — |
| 35 | S,S-di-n-propyl-N-ethyl phosphoroamidodithionite | 28.5 | 29.0 | 13.8 | 13.6 | — | — |
| 36 | S,S-di-n-propyl-N-n-butyl phosphoroamidodithionite | 20.7 | 20.5 | 10.0 | 10.0 | — | — |
| 37 | S,S-di-n-octyl-N-methyl phosphoroamidodithionite | 18.2 | 17.6 | 8.8 | 8.2 | — | — |
| 38 | S,S-di-n-octyl-N-piperidyl phosphoroamidodithionite | 15.8 | 14.8 | 7.6 | 7.2 | — | — |
| 39 | S,S-di-n-octyl-N-butyl phosphoroamidodithionite | 16.3 | 15.0 | 7.9 | 7.7 | — | — |
| 40 | S,S-di-n-propyl-N-acetyl-N-phenyl phosphoroamidodithionite | 20.3 | 21.3 | 9.9 | 10.4 | — | — |
| 41 | S,S-di-n-propyl-N-acetyl phosphoroamidodithionite | 26.8 | 26.3 | 13.0 | 12.1 | — | — |
| 42 | S,S-di-i-propyl-N-butyryl phosphoroamidodithionite | 24.0 | 23.6 | 11.6 | 11.5 | — | — |
| 43 | S,S-di-i-propyl-N-acetyl phosphoroamidodithionite | — | — | 12.9 | 11.8 | 0.0** | 0.19** |
| 44 | S,S-di-n-butyl-N-propionyl phosphoroamidodithionite | — | — | 10.5 | 10.9 | 4.7* | 3.2* |

*nitrogen
**halogen

The compounds of the present invention are, in general, herbicidal in both pre- and post-emergence applications. For pre-emergence control of undesirable vegetation these compounds will be applied in herbicidal quantities to the environment, e.g., soil infested with seeds and/or seedlings of such vegetation. Such application will inhibit the growth of or kill the seeds, germinating seeds and seedlings. For post-emergence applications the compounds of the present invention will be applied directly to the foliage and other plant parts. Generally they are effective against weed grasses as well as broadleaved weeds. Some may be selective with respect to type of application and/or type of weed.

Pre- and post-emergence herbicidal tests on representative compounds of this invention were made using the following methods:

PRE-EMERGENCE TEST

An acetone solution of the test compound was prepared by mixing 750 mg. compound, 220 mg. of a nonionic surfactant and 25 ml. of acetone. This solution was added to approximately 125 ml. of water containing 156 mg. of surfactant.

Seeds of the test vegetation were planted in a pot of soil and the compound solution was sprayed uniformly onto the soil surface at a dose of 100 micrograms per $cm^2$. The pot was watered and placed in a greenhouse. The pot was watered intermittently and was observed for seedling emergence, health of emerging seedlings, etc. for a 3-week period. At the end of this period the herbicidal effectiveness of the compound was rated based on the physiological observations. A 0 to 100 scale was used; 0 representing no phytotoxicity, 100 representing complete kill.

POST-EMERGENCE TEST

The test compound was formulated in the same manner as described above for the pre-emergence test. The concentration of the compound in this formulation was 5000 ppm. This formulation was uniformly sprayed on 2 replicate pots of 24-day-old plants (approximately 15 to 25 plants per pot) at a dose of 100 micrograms per cm$^2$. After the plants had dried, they were placed in a greenhouse and then watered intermittently at their bases as needed. The plants were observed periodically for phytotoxic effects and physiological and morphological responses to the treatment. After 3 weeks the herbicidal effectiveness of the compound was rated based on these observations. A 0 to 100 scale was used; 0 representing no phytotoxicity, 100 representing complete kill.

The results of these tests appear in Table II.

TABLE II

| Compound | Herbicidal Effectiveness - % | | | | | |
|---|---|---|---|---|---|---|
| | O | W | C | M | P | L |
| S,S-di-n-butyl-N,N-diethyl phosphoroamidodithionite | -/93 | 93/85 | 100/100 | -/100 | 100/100 | 100/100 |
| S,S-n-butyl-N,N-di-n-propyl phosphoroamidodithionite | -/100 | -/100 | -/100 | -/100 | -/100 | -/100 |
| S,S-di-n-butyl-N,N-dimethyl phosphoroamidodithionite | -/85 | -/85 | -/80 | -/95 | -/85 | -/65 |
| S,S-di-n-butyl phosphoroamidodithionite | 65/85 | -/90 | 90/- | 80/100 | — | -/75 |
| S,S-di-n-butyl-N-methyl phosphoroamidodithionite | -/95 | 70/80 | 100/75 | 95/100 | 90/- | 90/80 |
| S,S-di-n-butyl-N,N-di-n-butyl phosphoroamidodithionite | -/90 | -/75 | — | -/75 | — | — |
| S,S-diisopropyl-N,N-diethyl phosphoroamidodithionite | — | -/70 | — | -/90 | — | — |
| S,S-diisopropyl-N,N-di-n-propyl phosphoroamidodithionite | — | -/70 | — | -/60 | -/55 | — |
| S,S-di-n-butyl-N-2-fluorophenyl phosphoroamidodithionite | — | — | — | -/80 | -/95 | -/55 |
| S,S-diisopropyl-N,N-di-n-butyl phosphoroamidodithionite | — | — | — | -/100 | 75/- | -/70 |
| S,S-diisopropyl phosphoroamidodithionite | — | — | — | 80/- | 70/- | — |
| S,S-diisopropyl-N-methyl phosphoroamidodithionite | — | — | — | 70/- | 80/- | — |
| S,S-di-n-butyl-N-pyrrolidyl phosphoroamidodithionite | 95/100 | 70/75 | 100/- | 95/100 | -/100 | 90/90 |
| S,S-diisopropyl-N-ethyl phosphoroamidodithionite | — | 100/- | — | — | — | — |
| S,S-diisopropyl-N-n-butyl phosphoroamidodithionite | 100/- | 100/- | 80/- | -/90 | -/60 | -/60 |
| S,S-di-n-octyl-N-methyl phosphoroamidodithionite | — | — | — | -/70 | -/60 | — |
| S,S-di-n-octyl-N-piperidyl phosphoroamidodithionite | — | — | 75/- | — | — | — |
| S,S-diethyl-N,N-diethyl phosphoroamidodithionite | -/90 | -/90 | — | -/95 | -/95 | -/100 |
| S,S-diethyl-N,N-di-n-butyl phosphoroamidodithionite | -/80 | -/80 | -/90 | -/100 | -/95 | -/95 |
| S,S-diethyl-N,N-dimethyl phosphoroamidodithionite | — | -/70 | -/80 | -/80 | -/70 | -/100 |
| S,S-diethyl-N-ethyl phosphoroamidodithionite | — | — | 80/75 | -/100 | -/85 | -/100 |
| S,S-di-n-butyl-N-benzyl phosphoroamidodithionite | -/95 | -/90 | 100/90 | 95/100 | 95/100 | 95/100 |
| S,S-di-n-propyl-N-acetyl phosphoroamidodithionite | 100/- | 100/- | 100/- | 100/- | 100/- | 100/100 |
| S,S-di-i-propyl-N-butyryl phosphoroamidodithionite | — | — | — | 85/- | — | — |
| S,S-di-i-propyl-N-acetyl phosphoroamidodithionite | — | — | — | 100/- | 90/- | 85/- |
| S,S-di-n-propyl-N,N-diethyl phosphoroamidodithionite | -/95 | -/95 | -/95 | -/90 | -/100 | 100/100 |
| S,S-di-n-propyl-N-n-butyl phosphoroamidodithionite | -/100 | -/100 | -/95 | -/100 | -/100 | -/100 |
| S,S-di-n-propyl-N,N-dimethyl phosphoroamidodithionite | — | -/75 | — | -/80 | -/95 | -/100 |
| S,S-di-n-propyl-N-piperidyl phosphoroamidodithionite | -/85 | -/80 | 100/80 | -/100 | 95/100 | 95/100 |
| S,S-di-n-propyl-N-methyl phosphoroamidodithionite | 100/- | 80/85 | 100/90 | 100/100 | 100/100 | 100/100 |
| S,S-di-n-propyl-N,N-di-n-propyl phosphoroamidodithionite | -/90 | -/95 | 100/95 | -/100 | -/100 | 90/100 |
| S,S-di-n-propyl-N-benzyl phosphoroamidodithionite | — | 70/- | 100/- | 100/- | 100/- | 100/75 |
| S,S-di-n-propyl-N-allyl phosphoroamidodithionite | 100/- | — | 80/- | — | — | 95/- |
| S,S-di-n-propyl-N-ethyl phosphoroamidodithionite | 95/- | — | — | — | 90/- | — |
| S,S-di-n-butyl-N-propionyl phosphoroamidodithionite | — | -/75 | — | 80/90 | 80/- | — |
| S,S-di-n-butyl-N-acetyl | -/100 | -/100 | 100/100 | 100/100 | 70/100 | 80/100 |

TABLE II-continued

| Compound | | | Herbicidal Effectiveness - % | | | |
|---|---|---|---|---|---|---|
| | O | W | C | M | P | L |
| phosphoroamidodithionite | | | | | | |

O = Wild Oats (*Avena fatua*)
W = Watergrass (*Echinochloa crusgalli*)
C = Crabgrass (*Digitaria sanguinalis*)
M = Mustard (*Brassica arvensis*)
P = Pigweed (*Amaranthus retroflexus*)
L = Lamsquarter (*Chenopodium album*)

The amount of compound administered will vary with the particular plant part or plant growth medium which is to be contacted, the general location of application, i.e., sheltered areas such as greenhouses as compared to exposed areas such as fields, as well as the desired type of control. For pre-emergent control of most plants dosages in the range of about 0.5 to 20 lbs. per acre will be used. Such administration will give a concentration of about 2 to 80 ppm. compound distributed throughout 0.1 acre-foot. For post-emergence application, such as foliar spray application, compositions containing about 0.5 to 8 lbs. compound per 100 gal. spray will be used. Such application is equivalent to about 0.5 to 20 lbs. compound per acre.

The herbicidal compositions of this invention comprise a herbicidal amount of one or more of the above described compounds intimately admixed with a biologically inert carrier. The carrier may be a liquid diluent such as water or acetone or a solid. The solid may be in the form of dust powder or granules. These compositions will also usually contain adjuvants such as a wetting or dispersing agent to facilitate their penetration into the plant growth media or plant tissue and generally enhance their effectiveness. These compositions may also contain other pesticides, stabilizers, conditioners, fillers and the like.

The compounds of the present invention also possess insecticidal activity. Representative compounds were tested as follows to illustrate the insecticidal properties. The test results are reported in Table III.

TEST PROCEDURES

Two-spotted Mites (*Tetranychus urticae*):

An acetone solution of the candidate toxicant containing a small amount of nonionic emulsifier was diluted with water to 100 ppm. Pinto bean leaves which were infested with mites were dipped in the toxicant solution. Mortality readings were taken after 24 hours.

Two-spotted Mite Eggs (*Tetranychus urticae*):

An Acetone solution of the candidate toxicant was prepared containing a small amount of a nonionic surfactant. The acetone solution was diluted with water to give a 100 ppm solution. A primary leaf from Pinto beans which had been infested with mites 48 hours before and consequently contained mite eggs was immersed in the toxicant solution and then allowed to dry at room temperature for seven days at 85° F. On the eighth day the egg mortality was rated on a scale of 0 to 11; 0 representative no kill, 11 representing 100% kill.

Aphids (*Aphis gossypii* Glover):

An acetone solution of the candidate toxicant containing a small amount of nonionic emulsifier was diluted with water to 30 ppm. Cucumber leaves infested with the cotton aphids were dipped in the toxicant solution. Mortality readings were then taken after 24 hours.

TABLE III

| Compound | Two-spotted Mites | % Control Two-spotted Mites Eggs | Aphids |
|---|---|---|---|
| S,S-di-n-butyl-N,N-dimethyl phosphoroamidodithionite | 70 | 96 | — |
| S,S-n-butyl-N,N-di-n-propyl phosphoroamidodithionite | — | 100 | — |
| S,S-di-n-butyl phosphoroamidodithionite | — | 98 | — |
| S,S-di-n-butyl-N-methyl phosphoroamidodithionite | 99 | — | 99 |
| S,S-di-n-butyl-N-2-fluorophenyl phosphoroamidodithionite | — | 96 | — |
| S,S-diisopropyl-N-methyl phosphoroamidodithionite | 98 | — | — |
| S,S-diisopropyl-N-ethyl phosphoroamidodithionite | 100 | — | 96 |
| S,S-diethyl-N-ethyl phosphoroamidodithionite | 85 | — | — |
| S,S-di-n-propyl-N,N-diethyl phosphoroamidodithionite | 97* | — | 100 |
| S,S-di-n-propyl-N,N-dimethyl phosphoroamidodithionite | 100 | — | 100 |
| S,S-di-n-propyl-N-methyl phosphoroamidodithionite | 100 | 90 | 100 |
| S,S-di-n-propyl-N-piperidyl phosphoroamidodithionite | 100 | 96 | — |
| S,S-di-n-propyl-N,N-di-n-propyl phosphoroamidodithionite | 99 | 99 | — |
| S,S-di-n-propyl-N-benzyl phoshoroamidodithionite | 100 | 99 | — |
| S,S-di-n-propyl-N-allyl phoshoroamidodithionite | 99 | — | — |
| S,S-di-n-propyl-N-2-fluorophenyl phosphoroamidodithionite | 70 | 100 | — |
| S,S-di-n-propyl-N-ethyl phosphoroamidodithionite | 100 | 90 | 94 |

TABLE III-continued

| Compound | % Control | | |
| --- | --- | --- | --- |
| | Two-spotted Mites | Two-spotted Mites Eggs | Aphids |
| S,S-di-n-butyl-N-acetyl phosphoroamidodithionite | 96 | 96 | 94 |
| S,S-di-n-butyl-N-propionyl phosphoroamidodithionite | — | 98 | — |
| S,S-di-n-propyl-N-acetyl phosphoroamidodithionite | 100 | 100 | 100 |
| S,S-di-n-propyl-N-acetyl-N-phenyl phosphoroamidodithionite | 100 | — | 96 |

*40 ppm

In general, the preferred compounds for use as insecticides are those wherein $R_1$ and $R_2$ are individually propyl or butyl, $R_3$ is hydrogen, methyl, ethyl or propyl and $R_4$ is hydrogen, methyl, ethyl, propyl or fluorophenyl; or benzyl or allyl when $R_1$ and $R_2$ are propyl.

In addition to the specific formulations and application techniques described above, one or more of the compound derivatives of the invention may be applied in other liquid or solid formulations to the insects, their environment, or hosts susceptible to insect attack. For example, they may be sprayed or otherwise applied directly to plants or soil so as to effect control of insects coming into contact therewith.

Formulations of the compounds of this invention will comprise a toxic amount of one or more carbamate derivatives and a biologically inert carrier. Usually they will also contain a wetting agent. Solid carriers such as clay, talc, sawdust and the like may be used in such formulations. Liquid diluents which may be used with these compounds include water and aromatic solvents. In addition these formulations may contain other compatible pesticides, plant growth regulators, fillers, stabilizers, attractants and the like.

The concentration of the active ingredient to be used with inert carriers, either solid or liquid carriers, will be dependent upon many factors, such as the particular carbamate compound which is used, the carrier in or upon which it is incorporated, the method and conditions of application, the insect species to be controlled, etc., the proper consideration of these factors being within the skill of these versed in the art. In general, the toxic ingredients of this invention will be effective in concentrations from about 0.0001 percent by weight to as high as 90 percent by weight or higher. Economically, of course, it is desirable to use lower concentrations of this active ingredient. Thus, it is usually desirable to use less than 20 percent by weight of the active ingredient in a particular composition.

The terms "insecticide" and "insect" as used herein refer to their broad and commonly understood usage rather than to those creatures which in the strict biological sense are classified as insects. Thus, the term insect is used not only to include small invertebrate animals belonging to the class Insecta but also to other related classes of arthropods whose members are segmented invertebrates having more or fewer than six legs, such as spiders, mites, ticks, centipedes, worms and the like.

Some of the compounds of the present invention are also useful in the control of nematodes and algae, for example Euglena.

As will be evident to those skilled in the art, various modifications on this invention can be made or followed, in the light of the foregoing disclosure and discussion, without departing from the spirit or scope of the disclosure or from the scope of the following claims.

I claim:

1. A compound of the formula

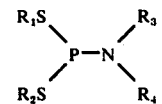

wherein $R_1$ and $R_2$ are independently alkyl of 1 to 8 carbon atoms or alkenyl of 2 to 8 carbon atoms, $R_3$ is hydrogen or alkyl of 1 to 4 carbon atoms and $R_4$ is alkenyl of 2 to 4 carbon atoms or aryl of 6 to 15 carbon atoms substituted with 0 to 5 halogen atoms of atomic number 9 to 35 or alkyl groups of 1 to 4 carbon atoms.

2. Compound of claim 1 wherein $R_1$ and $R_2$ are independently alkyl of 1 to 4 carbon atoms.

3. Compound of claim 1 wherein $R_1$ and $R_2$ are independently alkyl of 3 to 4 carbon atoms.

4. Compound of claim 1 wherein $R_4$ is phenyl substituted with 0 to 2 halogen atoms of atomic number 9 to 35 or alkyl of 1 to 2 carbon atoms.

5. Compound of claim 1 wherein $R_1$ and $R_2$ are the same and are alkyl of 1 to 4 carbon atoms, $R_3$ is hydrogen or alkyl of 1 to 4 carbon atoms, $R_4$ is phenyl substituted with 0 to 1 chlorine or fluorine atom.

6. Compound of claim 1 wherein $R_4$ is alkenyl of 2 to 4 carbon atoms.

* * * * *